United States Patent
Sullivan et al.

(10) Patent No.: US 9,730,865 B2
(45) Date of Patent: *Aug. 15, 2017

(54) APPLICATION AND USES OF PRG4 AND THERAPEUTIC MODULATION THEREOF

(75) Inventors: Benjamin Sullivan, San Diego, CA (US); Edward R. Truitt, San Diego, CA (US); David Sullivan, Boston, MA (US)

(73) Assignees: Lubris, LLC, Framingham, MA (US); Schepens Eye Research Institute, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,532

(22) PCT Filed: May 24, 2010

(86) PCT No.: PCT/US2010/035956
§ 371 (c)(1),
(2), (4) Date: Feb. 8, 2012

(87) PCT Pub. No.: WO2010/135736
PCT Pub. Date: Nov. 25, 2010

(65) Prior Publication Data
US 2012/0134925 A1    May 31, 2012

Related U.S. Application Data

(60) Provisional application No. 61/180,525, filed on May 22, 2009.

(51) Int. Cl.
| | | |
|---|---|---|
| A61B 17/24 | (2006.01) |
| A61K 8/02 | (2006.01) |
| A61L 27/50 | (2006.01) |
| A61K 8/64 | (2006.01) |
| A61K 8/73 | (2006.01) |
| A61K 9/00 | (2006.01) |
| A61K 31/728 | (2006.01) |
| A61Q 11/00 | (2006.01) |
| A61Q 19/00 | (2006.01) |
| A61K 36/886 | (2006.01) |
| A61K 38/17 | (2006.01) |
| C07K 14/47 | (2006.01) |
| C07K 14/435 | (2006.01) |
| A61K 9/68 | (2006.01) |

(52) U.S. Cl.
CPC .................. A61K 8/02 (2013.01); A61K 8/64 (2013.01); A61K 8/735 (2013.01); A61K 9/0014 (2013.01); A61K 9/0048 (2013.01); A61K 9/0063 (2013.01); A61K 31/728 (2013.01); A61K 36/886 (2013.01); A61K 38/1709 (2013.01); A61L 27/50 (2013.01); A61Q 11/00 (2013.01); A61Q 19/00 (2013.01); A61K 9/0041 (2013.01); A61K 9/0056 (2013.01); A61K 9/0058 (2013.01); C07K 14/435 (2013.01); C07K 14/47 (2013.01); C07K 14/4725 (2013.01); C07K 2317/41 (2013.01)

(58) Field of Classification Search
CPC ............ A61K 2300/00; A61K 38/1709; A61K 31/728; A61K 31/715; A61K 9/0048; A61K 8/64; A61K 9/0056; A61K 9/0058; A61K 31/70; A61K 31/726
See application file for complete search history.

(56) References Cited

U.S. PATENT DOCUMENTS

| | | | |
|---|---|---|---|
| 4,438,100 A * | 3/1984 | Balslev | A01N 59/00 424/537 |
| 4,938,963 A * | 7/1990 | Parnell | 424/440 |
| 5,326,558 A | 7/1994 | Turner et al. | |
| 6,433,142 B1 | 8/2002 | Turner et al. | |
| 6,743,774 B1 | 6/2004 | Jay | |
| 6,960,562 B2 | 11/2005 | Jay | |
| 7,001,881 B1 | 2/2006 | Jay | |
| 7,030,223 B2 | 4/2006 | Turner et al. | |
| 7,361,738 B2 | 4/2008 | Turner et al. | |
| 7,415,381 B2 | 8/2008 | Jay | |
| 7,618,941 B2 | 11/2009 | Jay | |
| 8,026,346 B2 | 9/2011 | Jay | |
| 8,506,944 B2 | 8/2013 | Sullivan et al. | |
| 8,551,467 B2 | 10/2013 | Sullivan et al. | |
| 8,563,028 B2 | 10/2013 | Sullivan et al. | |
| 8,680,057 B2 | 3/2014 | Jay | |
| 8,945,604 B2 | 2/2015 | Sullivan et al. | |
| 8,980,840 B2 | 3/2015 | Truitt, III et al. | |
| 9,044,500 B2 | 6/2015 | Kawa et al. | |
| 9,107,885 B2 | 8/2015 | Sullivan et al. | |

(Continued)

FOREIGN PATENT DOCUMENTS

GB    2361870 A * 7/2001 ............... A61K 7/16

OTHER PUBLICATIONS

S-Gravenmade et al. The effect of mucin-containing artificial saliva on severe xerostomia. Int J Oral Surg. 1974;3(6):435-9.*

(Continued)

*Primary Examiner* — Satyanarayana R Gudibande
*Assistant Examiner* — Jia-Hai Lee
(74) *Attorney, Agent, or Firm* — Goodwin Procter LLP

(57) ABSTRACT

The present invention relates to the uses of the protein PRG4 and therapeutic modulation thereof. In particular, the present invention relates compositions and methods utilizing PRG4 and therapeutic modulation thereof, including, use as a surgical lubricant, use in a treatment for prevention or reduction of post-surgical adhesions, use in a treatment for oral ulcerations, use as an athletic lubricating patch, use as a dermal filler, use in a treatment for dry mouth, use in a drug delivery method or composition, and use in nursing lubrication.

12 Claims, 2 Drawing Sheets

(56) References Cited

U.S. PATENT DOCUMENTS

| | | |
|---|---|---|
| 9,138,457 B2 | 9/2015 | Sullivan et al. |
| 9,248,161 B2 | 2/2016 | Sullivan et al. |
| 9,393,285 B2 | 7/2016 | Sullivan et al. |
| 9,421,241 B2 | 8/2016 | Sullivan et al. |
| 2003/0180948 A1 | 9/2003 | Hutchins et al. |
| 2004/0229804 A1 | 11/2004 | Jay |
| 2006/0025570 A1 | 2/2006 | Turner et al. |
| 2006/0240037 A1 | 10/2006 | Fey et al. |
| 2007/0111327 A1 | 5/2007 | Jay |
| 2007/0191268 A1* | 8/2007 | Flannery et al. ........ 514/12 |
| 2007/0249557 A1 | 10/2007 | Jay |
| 2007/0275032 A1 | 11/2007 | Wimmer et al. |
| 2008/0139458 A1 | 6/2008 | Jay et al. |
| 2008/0177218 A1 | 7/2008 | McKay et al. |
| 2008/0287369 A1 | 11/2008 | Jay |
| 2009/0068247 A1 | 3/2009 | Jay |
| 2009/0104148 A1 | 4/2009 | Jay et al. |
| 2009/0155200 A1 | 6/2009 | Jay |
| 2010/0204087 A1 | 8/2010 | Jay |
| 2012/0052077 A1 | 3/2012 | Truitt, III et al. |
| 2013/0039865 A1 | 2/2013 | Truitt, III et al. |
| 2013/0116186 A1 | 5/2013 | Jay |
| 2013/0315973 A1 | 11/2013 | Jay |
| 2014/0179611 A1 | 6/2014 | Jay |
| 2016/0101149 A1 | 4/2016 | Sullivan et al. |
| 2016/0235809 A1 | 8/2016 | Sullivan et al. |
| 2016/0250286 A1 | 9/2016 | Schmidt |
| 2016/0304572 A1 | 10/2016 | Schmidt et al. |

OTHER PUBLICATIONS

Irwin D. Mandel. A Contemporary View of Salivary Research. Crit Rev Oral Biol Med. 1993;4(3-4):599-604.*

Flannery et al. Articular cartilage superficial zone protein (SZP) is homologous to megakaryocyte stimulating factor precursor and Is a multifunctional proteoglycan with potential growth-promoting, cytoprotective, and lubricating properties in cartilage metabolism. Biochem Biophys Res Commun. Jan. 27, 1999;254(3):535-41.*

Scully et al. Adverse drug reactions in the orofacial region. Crit Rev Oral Biol Med. 2004; 15(4):221-240.*

Jiang et al. Bovine submaxillary mucin contains multiple domains and tandemly repeated non-identical sequences. Biochem. J. (1998) 331, 193-199.*

Abu-Lail et al. "Friction Reducing Properties of Lubricin (PRG4): A Nanoscale Study of Chondroprotection" European Cells and Materials vol. 12. Suppl. 1, 2006 (p. 48).

Fox et al. " Xerostomia: evaluation of a symptom with increasing significance" The Journal of the American Dental Association Apr. 1, 1985 vol. 110 No. 4 519-525. (abstract only).

International Search Report for PCT/US2010/035956, mailed Feb. 28, 2011, 5 pages.

Supplementary Extended European Search Report from the European Patent Office for European App. No. 10 77 8522.2 dated Jul. 1, 2013—National Phase of PCT/US2010/035956, related to present application.

Fleenor, et al., "TGFbeta2-induced changes in human trabecular meshwork: implications for intraocular pressure", Invest Ophthalmol Vis Sci. Jan. 2006;47(1):226-34, PubMed.

Ikegawa, et al., "Isolation, characterization and mapping of the mouse and human PRG4 (proteoglycan 4) genes", Cytogenet Cell Genet. 2000;90(3-4):291-7.

Jay et al., "The role of lubricin in the mechanical behavior of synovial fluid", PNAS, vol. 104, No. 15, Apr. 10, 2007, (6 pages).

Rhee, et al., "The secreted glycoprotein lubricin protects cartilage surfaces and inhibits synovial cell overgrowth", The Journal of Clinical Investigation, vol. 115, No. 3, Mar. 2005 (10 pages).

* cited by examiner

| Lane # ||
|---|---|
| 1- DNA Markers | 9- DNA Markers |
| 2- No Template Control | 10- No Template Control |
| 3- Female 1 Lacrimal | 11- Female 1 Submandibular |
| 4- Female 2 Lacrimal | 12- Female 2 Submandibular |
| 5- Female 3 Lacrimal | 13- Female 3 Submandibular |
| 6- Male 1 Lacrimal | 14- Male 1 Submandibular |
| 7- Male 2 Lacrimal | 15- Male 2 Submandibular |
| 8- Male 3 Lacrimal | 16- Male 3 Submandibular |

FIGURE 2

SEQ ID NO:1
MAWKTLPIYLLLLLSVFVIQQVSSQDLSSCAGRCGEGYSRDATCNCDYNCQHYMEC
CPDFKRVCTAELSCKGRCFESFERGRECDCDAQCKKYDKCCPDYESFCAEVHNPTSP
PSSKKAPPPSGASQTIKSTTKRSPKPPNKKKTKKVIESEEITEEHSVSENQESSSSSSSSS
SSSTIRKIKSSKNSAANRELQKKLKVKDNKKNRTKKKPTPKPPVVDEAGSGLDNGDF
KVTTPDTSTTQHNKVSTSPKITTAKPINPRPSLPPNSDTSKETSLTVNKETTVETKETTT
TNKQTSTDGKEKTTSAKETQSIEKTSAKDLAPTSKVLAKPTPKAETTTKGPALTTPKE
PTPTTPKEPASTTPKEPTPTTIKSAPTTPKEPAPTTTKSAPTTPKEPAPTTTKEPAPTTPK
EPAPTTTKEPAPTTTKSAPTTPKEPAPTTPKKPAPTTPKEPAPTTPKEPTPTTPKEPAPTT
KEPAPTTPKEPAPTAPKKPAPTTPKEPAPTTPKEPAPTTTKEPSPTTPKEPAPTTTKSAP
TTTKEPAPTTTKSAPTTPKEPSPTTTKEPAPTTPKEPAPTTPKKPAPTTPKEPAPTTPKEP
APTTTKKPAPTTPKEPAPTTPKETAPTTPKKLTPTTPEKLAPTTPEKPAPTTPEELAPTT
PEEPTPTTPEEPAPTTPKAAAPNTPKEPAPTTPKEPAPTTPKEPAPTTPKETAPTTPKGT
APTTLKEPAPTTPKKPAPKELAPTTTKEPTSTTCDKPAPTTPKGTAPTTPKEPAPTTPKE
PAPTTPKGTAPTTLKEPAPTTPKKPAPKELAPTTTKGPTSTTSDKPAPTTPKETAPTTPK
EPAPTTPKKPAPTTPETPPPTTSEVSTPTTTKEPTTIHKSPDESTPELSAEPTPKALENSP
KEPGVPTTKTPAATKPEMTTTAKDKTTERDLRTTPETTTAAPKMTKETATTTEKTTES
KITATTTQVTSTTTQDTTPFKITTLKTTTLAPKVTTTKKTITTTEIMNKPEETAKPKDRA
TNSKATTPKPQKPTKAPKKPTSTKKPKTMPRVRKPKTTPTPRKMTSTMPELNPTSRIA
EAMLQTTTRPNQTPNSKLVEVNPKSEDAGGAEGETPHMLLRPHVFMPEVTPDMDYL
PRVPNQGIIINPMLSDETNICNGKPVDGLTTLRNGTLVAFRGHYFWMLSPFSPPSPARR
ITEVWGIPSPIDTVFTRCNCEGKTFFFKDSQYWRFTNDIKDAGYPKPIFKGFGGLTGQI
VAALSTAKYKNWPESVYFFKRGGSIQQYIYKQEPVQKCPGRRPALNYPVYGETTQVR
RRRFERAIGPSQTHTIRIQYSPARLAYQDKGVLHNEVKVSILWRGLPNVVTSAISLPNI
RKPDGYDYYAFSKDQYYNIDVPSRTARAITTRSGQTLSKVWYNCP

SEQ ID NO:2: GATGCAGGGTACCCCAAA (human, sense)
SEQ ID NO:3: CAGACTTTGGATAAGGTCTGCC (human, antisense)

APPLICATION AND USES OF PRG4 AND THERAPEUTIC MODULATION THEREOF

CROSS-REFERENCE

This application is a 35 U.S.C. §371 U.S. National Stage application of International Patent Application No. PCT/US2010/35956, filed Jan. 13, 2010, and claims the benefit of U.S. Provisional Application No. 61/180,525, filed May 22, 2009 which applications are incorporated herein by reference in their entirety.

The instant application contains a Sequence Listing which has been submitted electronically in ASCII format and is hereby incorporated by reference in its entirety. Said ASCII copy, created on Jan. 26, 2017, is named LUB-016_SL.txt and is 13,199 bytes in size.

FIELD OF THE INVENTION

The present invention relates to the uses of the protein PRG4 (including proteoglycans thereof) and/or therapeutic modulation thereof. In particular, the present invention relates compositions and methods thereof, including, surgical lubrication, athletic lubrication, treatment of diseases associated with compromised boundary lubrication in the oral cavity, a dermal filler, methods of drug delivery, and for nursing lubrication.

BACKGROUND

The proteoglycan 4 (prg4) gene codes for highly glycosylated proteins termed megakaryocyte stimulating factor (MSF), lubricin, and superficial zone protein (SZP). Lubricin was first isolated from synovial fluid and demonstrated lubricating ability in vitro similar to synovial fluid at a cartilage-glass interface. Lubricin was later identified as a product of synovial fibroblasts. O-linked β(1-3)Gal-GalNAc oligosaccharides within a large mucin like domain of 940 amino acids, encoded for by exon 6, have also been described. SZP was first localized at the surface of explant cartilage from the superficial zone and isolated from conditioned medium. These molecules (as well as O-linked proteoglycans thereof) are collectively referred to herein as PRG4. PRG4 has been shown to be present inside the body at the surface of synovium, tendon, and meniscus, but there has been no description of using PRG4 as a lubricant for the purposes described herein.

SUMMARY OF THE INVENTION

The present invention provides, in various embodiments, compositions, and methods of use thereof, for managing lubrication. In various embodiments, such lubrication includes, by way of non-limiting example, use as a surgical lubricant, use in a treatment for prevention or reduction of post-surgical adhesions, use in a treatment for oral ulcerations, use as an athletic lubricating patch, use as a dermal filler, use in a treatment for dry mouth, use in a drug delivery method or composition, and use in nursing lubrication. Also, provided herein is PRG4 protein (e.g., purified or isolated PRG4 protein) for use in the treatment of any of the aforementioned disorders (or any other disorder described herein).

In one embodiment, such compositions and methods are provided for the therapeutic replenishment and enrichment of boundary lubricant molecules in the oral cavity. Described in certain embodiments of the present invention is the observation that PRG4 mRNA is expressed in mouse Submandibular tissue, indicating that PRG4 protein is secreted into the oral cavity. FIG. 1 illustrates PRG4 mRNA expression in various mouse submandibular glands. Amplified samples were screened for the presence of PRG4 products by using agarose gel electrophoresis. Vertical lanes 11-16 contain amplified, verified PRG4 mRNA from submandibular gland tissues of 6 different mice.

Described in certain instances of the present invention is the observation that the PRG4 protein protects the oral cavity (including the throat) against significant shear forces generated during eating, talking, swallowing, speaking and/or other oral functions. Further described in certain instances of the present invention is the observation that the molecular mechanisms of boundary lubrication found in cartilage, including the ability of secreted components to mediate shear stress in the presence of dynamic loading, are likely useful when utilized for lubricating the oral cavity.

In certain embodiments, the present invention provides an oral care composition suitable for topical application to the oral cavity of a patient of a preparation containing a therapeutic amount of a therapeutically effective concentration of a PRG4 protein (including e.g., a PRG4 proteins that is glycosylated, e.g., an O-linked proteoglycan). In some embodiments, the oral care pharmaceutical composition comprises PRG4 protein suspended in a aqueous osmotically balanced salt solution, multiphasic emuslification, a gel, liquid, cream, ointment, spray, viscous solution or encapsulated within slow-release devices, or in a lozenge.

In certain embodiments, the oral care composition of the present invention further comprises, various oil extracts, sweeteners, salivary gland stimulators, preservatives and flavorings. In certain embodiments the oral care composition further comprises a therapeutically effective amount of sodium hyaluronate. In certain embodiments, the oral care composition will further comprise a local anesthetic such as lidocaine, lignocaine or prilocaine.

The present invention provides a method for treating xerostomia, or symptoms associated therewith (including symptoms of xerostomia associated with Sjögren's syndrome, allergy, oral surface disorders, chronic inflammation, hyperosmolarity, aging, prescription or OTC drugs, radiation therapy, chemotherapy, nerve damage or any combination thereof) comprising topically administering to the oral cavity (or an ulcer within the oral cavity) in an individual in need thereof, an effective amount of any oral care composition described herein. In a further embodiment, the present invention provides a method for treating oral ulcerations comprising topically administering to an oral cavity ulcer in an individual in need thereof, an effective amount of the oral care composition of the present invention.

Certain embodiments of the present invention provide a lubricant composition suitable for use during medical and surgical procedures including, by way of non-limiting example: the insertion of catheters, endoscopes, surgical instruments, gloves into body orifices, as surgical auxiliaries and/or temporary implants, as hydration implants, and for use in cataract extraction, photokeratectomy, Intraocular Lens (IOL) insertion and removal, corneal surgery, glaucoma surgery, trauma surgery, posterior segment surgery, ocular plastic surgery and muscle surgery comprising PRG4 in a surgically acceptable salt solution.

In certain embodiments, any lubricant composition described herein further comprises sodium hyaluronate. In certain embodiments, the lubricant composition of the present invention further comprises additional excipients and demulcents, including but not limited to carboxymethylcellulose sodium, hydroxyethyl cellulose, hypromellose, methylcellulose, dextran 70, gelatin, glycerin, polyethylene glycol 300, polyethylene glycol 400, polysorbate 80, propylene glycol, polyvinyl alcohol and povidone. In certain embodiments, any lubricant composition described herein further comprises one or more local anesthetic's selected from the group consisting of lidociane, lignocaine and prilocaine. In certain embodiments, any lubricant composition described herein further comprises one or more antiseptics selected from the group consisting of chlorhexidine gluconate, benzalkonium chloride, cetyl trimethylammonium bromide, cetylpyridinium chloride, benzethonium chloride, alcohol, sodium chloride and sodium bicarbonate.

Certain embodiments of the present invention provide a method of providing lubrication for use in surgery or medical procedures comprising the topical application of any lubricating composition described herein to any medical instrument or other surface involved in the procedure. In various embodiments, the surgical or medical procedures include, by way of non-limiting example, the insertion of catheters, endoscopes, surgical instruments, gloves into body orifices, as surgical auxiliaries and/or temporary implants, as hydration implants, and for use in cataract extraction, photokeratectomy, Intraocular Lens (IOL) insertion and removal, corneal surgery, glaucoma surgery, trauma surgery, posterior segment surgery, ocular plastic surgery and muscle surgery.

Some embodiments of the present invention provide a method of preventing or reducing friction during ambulatory motion comprising the application of any suitable lubricating composition described herein (e.g., an aqueous gel, sol, solution, or adhesive patch containing PRG4) to the area of interest. In certain embodiments of the present invention the composition (e.g., adhesive patch) further comprises hyaluronic acid. In certain embodiments of the present invention the composition (e.g., adhesive patch) further comprises a residence time increasing polymer, excipient or demulcent.

Certain embodiments of present invention provide a dermatological composition suitable for use as a injectable dermal filler comprising a dermatologically effective concentration of PRG4 in combination with (e.g., suspended in) a dermatologically acceptable medium or vehicle (e.g., a viscous solution). In certain embodiments a dermatological composition of the present invention further comprises a dermatologically effective amount of hyaluronic acid. In one embodiment, the dermatological use is to reduce the appearance of scar tissue.

In certain embodiments any dermatological composition of the present invention further comprises a dermatologically effective amount of collagen, carboxymethyl cellulose, polyethylene glycol and/or polyethylene oxide. In certain embodiments any dermatological composition of the present invention further comprises a drug selected from the group consisting of antithrombogenic drugs, anti-inflammatory drugs, hormones, chemotactic factors, analgesics, growth factors, cytokines, osteogenic factors and anesthetics. In certain embodiments any dermatological composition of the present invention further comprises retinoic acid and/or deuterium reduced water.

Some embodiments of the present invention provide a method for restoring of tissue volume, skin turgor, texture and tightness in the skin (e.g., in the face or selected areas of the body) of a person comprising the steps of injecting a dermatological composition of the present invention into the dermis, or the hypodermis. In various embodiments, treatment and injection may occur at one or more areas of the face, or selected areas of the body of a person, including, but not limited to, the peri-orbital area, the lips, the malar area, the nasolabial folds, the labio-mandibular folds, the neck, or the hands.

Certain embodiments of the present invention provide a method of providing (e.g., facilitating) drug delivery, the method comprising delivering a bioactive agent to an individual, the bioactive agent being delivered in a composition comprising: an admixture of a bioactive agent and a carrier comprising PRG4.

In certain embodiments of the present invention, the bioactive agent comprises a drug, a peptide, a protein, an antibody or fragment thereof, a nucleic acid, or imaging agent. In another embodiment, the delivery carrier further comprises sodium hyaluronate. In certain embodiments of the present invention, the delivery carrier further comprises a surface active phospholipid selected from the group consisting of L-α-dipalmitoylphosphatidylcholine, phosphatidylcholine, phosphatidylethanolamine and sphingomyelin. The physical delivery of the admixture can be accomplished via by topical administration, injection, or orally, or by any other suitable administration technique.

Some embodiments of the present invention provide a method of preventing or reducing friction during nursing (breastfeeding) comprising applying to a surface in need thereof (e.g., a nipple, areola and/or breast) any lubricating composition described herein (e.g., an aqueous gel, sol, solution, or adhesive patch) containing PRG4. In certain embodiments of the present invention any composition described herein (e.g., adhesive patch) further comprises hyaluronic acid, lanolin, glycerin, or the like. In certain embodiments of the present invention any composition (e.g., adhesive patch) further comprises a residence time increasing polymer, excipient or demulcent.

INCORPORATION BY REFERENCE

All publications and patent applications mentioned in this specification are herein incorporated by reference for the purpose cited.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates an amino acid sequence of PRG4 as well as nucleic acid primer sequences for PCR amplification of the PRG4 mRNA.

DETAILED DESCRIPTION OF THE INVENTION

Figure 1:
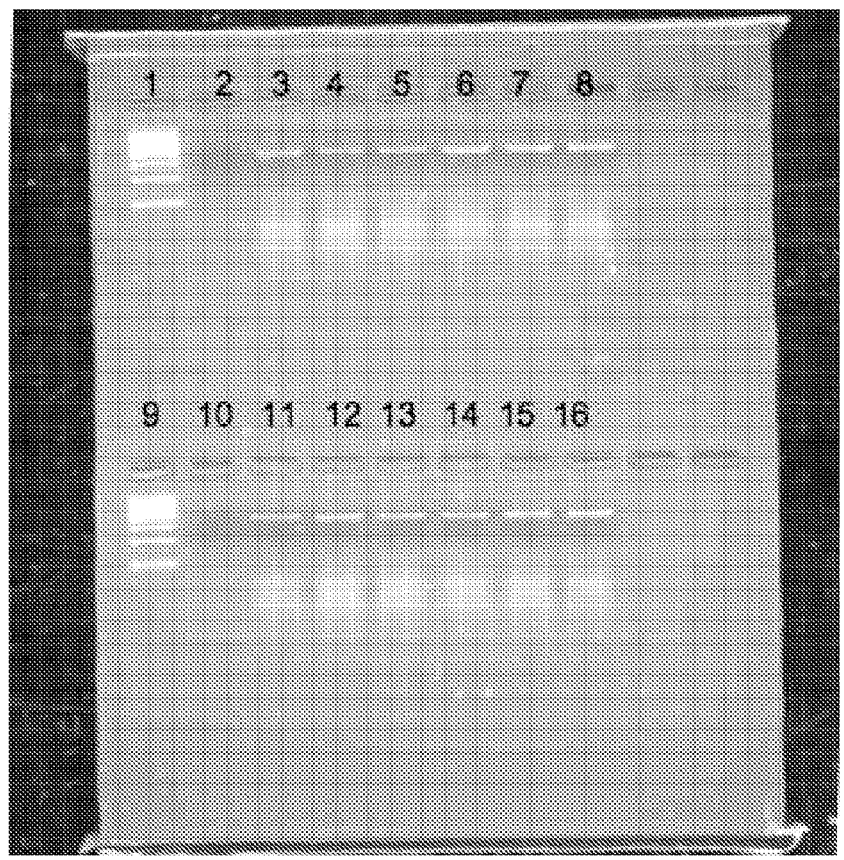
FIG. 1 illustrates mouse PRG4 mRNA expression, as demonstrated by agarose electrophoresis following amplification in Submandibular gland tissue. mRNA was verified through sequencing.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The functional importance of PRG4 was shown by mutations that cause the camptodactyly-arthropathy-coxa vara-pericarditis (CACP) disease syndrome in humans. CACP is manifest by camptodactyly, noninflammatory arthropathy, and hypertrophic synovitis, with coxa vara deformity, pericarditis, and pleural effusion. Also, in PRG4-null mice, cartilage deterioration and subsequent joint failure were observed. Therefore, PRG4 expression is a necessary component of healthy synovial joints.

PRG4 is a member of the mucin family, which are generally abundant on epithelial linings and provide many functions, including lubrication and protection from invading microorganisms. The functional properties of mucins are generally determined by specialized glycosylation patterns and their ability to form multimers through intermolecular disulfide bonds, both of which are altered in chronic diseases (e.g. cystic fibrosis, asthma). Biochemical characterization of PRG4 isolated from synovial fluid showed molecular heterogeneity in O-glycosylation, which appears to mediate lubricating properties. Preliminary data on PRG4 from bovine synovial fluid has revealed the presence of disulfide-bonded dimers, in addition to the monomeric forms, predicted from the conserved cysteine-rich domains at both N- and C-terminals, along with an unpaired cysteine at the C-terminal.

Physicochemical modes of lubrication have been classified as fluid film or boundary. The operative lubrication modes depend on the normal and tangential forces on the articulating tissues, on the relative rate of tangential motion between these surfaces, and on the time history of both loading and motion. The friction coefficient, $\mu$, provides a quantitative measure, and is defined as the ratio of tangential friction force to the normal force. One type of fluid-mediated lubrication mode is hydrostatic. At the onset of loading and typically for a prolonged duration, interstitial fluid becomes pressurized, due to the biphasic nature of tissue; fluid may also be forced into the asperities between articular surfaces through a weeping mechanism. Pressurized interstitial fluid and trapped lubricant pools may therefore contribute significantly to the bearing of normal load with little resistance to shear force, facilitating a very low $\mu$. Also, at the onset of loading and/or motion, squeeze film, hydrodynamic, and elastohydrodynamic types of fluid film lubrication occur, with pressurization, motion, and deformation acting to drive viscous lubricant from and/or through the gap between two surfaces in relative motion.

In some instances, the relevant extent to which fluid pressure/film versus boundary lubrication occurs depends on a number of factors. When lubricant film can flow between the conforming sliding surfaces, which can deform elastically, elastohydrodynamic lubrication occurs. Pressure, surface roughness, and relative sliding velocity determine when full fluid lubrication begins to break down and the lubrication enters new regimes. As velocity decreases further, lubricant films adherent to the articulating surfaces begin to contribute and a mixed regime of lubrication occurs. If the velocity decreases even further and only an ultra-thin lubricant layer composed of a few molecules remain, boundary lubrication occurs. In certain instances, a boundary mode of lubrication is therefore indicated by a friction coefficient (ratio of the measured frictional force between two contacting surfaces in relative motion to the applied normal force) during steady sliding being invariant with factors that influence formation of a fluid film, such as relative sliding velocity and axial load. For certain tissues in the body, such as articular cartilage, it has been concluded that boundary lubrication occurs, and is complemented by fluid pressurization and other mechanisms. Use of agents for boundary lubrication for the purposes and uses described in the present invention have not been previously pursued, however, because, e.g., the dominant modes of lubrication have been assumed to be hydrodynamic and elastohydrodynamic. Moreover, products created for the applications proposed herein treatments have traditionally focused on viscous fluid phase lubrication or hydration with long chain polymers such as polycarbophils, polyethylene glycols, and glycerin. Examples of fluid film approaches include, Biotene, Orex, Salivart for xerostomia, Blistex for oral ulcerations, Surgilube and Healon for surgical applications, and Restylane and JuveDerm for dermal fillers. For the invention claimed herein, optimal lubrication can encompass an enhanced boundary mode or involve a combination of an enhanced boundary mode and fluid film lubrication.

In boundary lubrication, load is supported by surface-to-surface contact, and the associated frictional properties are determined by lubricant surface molecules. In certain instances, this mode may be important because the opposing tissue surface make contact over ~10% of the total area, and this may be where most of the friction occurs. Furthermore, in some instances, with increasing loading time and dissipation of hydrostatic pressure, lubricant-coated surfaces bear an increasingly higher portion of the load relative to pressurized fluid, and consequently, this mode can become increasingly dominant. In certain instances, boundary lubrication mitigates stick-slip, and is therefore manifest as decreased resistance both to steady motion and the start-up of motion. In some instances, the latter situation is relevant to load bearing surfaces after prolonged compressive loading (e.g., sitting or standing in vivo). Typical wear patterns of articular surfaces, such as in cartilage, also illustrate that in some instances, boundary lubrication is important for the protection and maintenance of the tissue structure. In some instances, the loading of the oral cavity is subject to (e.g., dominated by) shear forces, with chewing generating significant stress upon surface cells and tooth enamel. Moreover, in disease states that down regulate production of lubricants within the oral cavity or act to atrophy epithelial cells, routine shear stress may also pose a strong degradatory and inflammatory risk. Severe atrophy or iatrogenically caused dryness from cancer treatments such as tamoxifen, antihistamines, anti-depressants, or high blood pressure medication may also make normal levels of shear stress painful.

In some instances, the accumulation of PRG4 within fluid between articulating surfaces, as well as its propensity to spontaneously bind to tissue matrix, contribute to PRG4's boundary lubricating ability.

In certain embodiments described herein, we disclose that proteoglycan 4 (PRG4) plays a role as a boundary lubricant along the walls of the oral cavity. In some embodiments, this glycoprotein (PRG4) protects oral surfaces against frictional forces, cell adhesion and/or protein deposition. Any one or more of various native and recombinant lubricin proteins and isoforms are utilized in various embodiments described herein. For instance, U.S. Pat. Nos. 5,326,558; 6,433,142; 7,030,223, and 7,361,738 disclose a family of human megakaryocyte stimulating factors (MSFs), each of which is incorporated herein for such disclosure. U.S. Pat. Nos.

6,960,562 and 6,743,774 also disclose a lubricating polypeptide, tribonectin, comprising a substantially pure fragment of MSF, each of which is incorporated herein for such disclosure.

Oral Care

Provided in certain embodiments herein, is a method of managing oral cavity lubrication deficiency, xerostomia, or symptoms associated therewith (including symptoms of xerostomia associated with Sjögren's syndrome, allergy, oral surface disorders, chronic inflammation, hyperosmolarity, aging, prescription or OTC drugs, radiation therapy, chemotherapy, nerve damage or any combination thereof) in an individual in need thereof comprising administering to the oral cavity of the individual PRG4 protein (e.g., in an effective amount). In some embodiments, the PRG4 protein is administered in an oral care composition (e.g., a pharmaceutically acceptable oral care composition). In certain embodiments, the administered PRG4 protein is an exogenous PRG4 protein (i.e., PRG4 that is not native to the individual to whom it is being administered). In some embodiments, an orally acceptable formulation (e.g., an oral care product described herein) comprises a demulcent, an astringent, an emollient, a sweetener, a stimulator, or combinations thereof. In another embodiment any composition described herein further comprises a therapeutically effective amount of sodium hyaluronate.

Xerostomia is a condition in which the salivary glands do not produce sufficient quantities of saliva. In certain instances, xerostomia causes discomfort which can in some cases be quite severe. Without saliva, the mouth may burn and the throat and tongue can undergo radical changes. Teeth can decay rapidly and the tongue can become smooth, cracked and vulnerable to infection. There is often a loss of taste and, because saliva contains important digestive enzymes, there are often problems with digestion. The mouth is one of the body areas most exposed to the external environment. Normally, mucous forms a continuous protective layer in the nose, mouth and throat. A patient suffering from xerostomia not only has decreased fluid in the mouth, but may also have an insufficient quantity of mucoproteins and mucopolysaccharides to hold fluid in contact with the cells and create a barrier to irritation and infection. Provided in certain embodiments herein are methods of treating xerostomia or any symptom associated therewith (specifically including the aforementioned symptoms), the method comprising orally administering to an individual in need thereof PRG4 protein (e.g., an oral care composition comprising PRG4 protein in an effective amount and/or concentration).

It is estimated that several million individuals suffer from this condition nationwide. The actual number of individuals suffering from xerostomia is not known, however, because until recently there has been little acknowledgement of the prevalence or severity of the problem. Cases of xerostomia may vary from the mild, in which only slight dryness is experienced, to severe cases in which the patient will have serious problems with mastication, swallowing, digestion, speech, and the like. As noted in U.S. Pat. No. 4,438,100 to Balslev et al., there are a number of causes of xerostomia, including the physiological (e.g., age, menopause, postoperative conditions, dehydration), as well as the psychic (nervousness). The reasons for mouth dryness may also be pharmacological (e.g., as a common side effect of many medications, including diuretics, anti-arthritics and anti-depressants) or as a result of radiotherapy. The most severe cases of xerostomia are caused by radiation therapy after head and neck surgery and by autoimmune diseases such as lupus, Sjogrens Syndrome, and rheumatoid arthritis. See, for example, P. C. Fox et al., J. Am. Dental Assoc. 110:519-525 (1985).

Current treatments for xerostomia have significant drawbacks. For example, symptoms of mild xerostomia can be somewhat alleviated by consumption of fluids, hard candy and throat lozenges. Because of the susceptibility of xerostomia patients to tooth decay and gum disease, however, the increased sugar intake associated with conventional candy and lozenges is of real concern. In addition, fluids or candy are typically not effective with more severe cases of xerostomia, nor do they provide long-lasting relief with mild cases.

There are also a number of artificial salvias on the market which contain alcohol, mineral oils, glycerine, and combinations of polyethylene glycols. A number of carboxymethylcellulose-based preparations are on the market as well, including those sold under the marks Orex® (Young Dental), Xero-Lube® (Scherer), Moi-Stir® (Kingswood Laboratories), and Salivart® (Westport Pharmaceuticals). Many patients find, however, that such preparations are irritating or distasteful, and that their lubricating effect is of relatively short duration.

Xerostomia and symptoms associated therewith can be determined by any suitable method. In some instances, a deficiency in oral lubrication and symptoms associated therewith is defined either qualitatively (e.g., a feeling of low lubrication, discomfort, oral dryness, oral itch or a burning sensation, painful mastication, and difficulty speaking or quantitatively (e.g., measured through mechanical, biochemical, electrical, optical or other methods of quantitative assays).

In a preferred embodiment, the composition is administered as an aqueous solution (or suspension) of PRG4. In certain embodiments the composition will further comprise yerba santa fluid extract, citrus oil, lemon oil, lime oil, neroli oil, orange oil, a mint oil, peppermint oil, spearmint oil, anise oil, cardamom oil, cinnamon oil, clove oil, coriander oil, eucalyptus oil, fennel oil, lemongrass oil, nutmeg oil, eriodictyon fluid extract, or glycyrrhiza extract in the range of 0.25 wt. % to 10 wt. %, more preferably 0.5 wt. % to 5.0 wt. %, and most preferably about 1.25 wt. %. In certain emboidments the composition will further comprise one or more sweeteners, in total comprising about 1.0 wt. % to 30 wt. %, more preferably 10 wt. % to 20 wt. %, most preferably about 15 wt. % sweetener.

Suitable sweeteners may be readily selected, and the amount of sweetener incorporated into the present composition will be determined by taste. Generally, the sweetener may be any compound or compounds that cause sweetness or intensify sweetness. The sweetener may be of naturally occurring or synthetic origin, and may have nutritive or non-nutritive value. Examples of suitable sweeteners for use herein include: the saccharides, e.g., fructose, glucose, glycerone, threose, erythrose, methylpentose, galactose, xylose, ribose, dextrose, maltose and d-mannose; sugar alcohols such as sorbitol, xylitol and mannitol; water-soluble artificial sweeteners such as the soluble saccharin salts, e.g., sodium or calcium saccharin, cyclamate salts, acesulfame-K, and the like; and dipeptide-based sweeteners such as L-aspartyl-L-phenylalanine methyl ester. Other examples of suitable sweeteners are set forth in the Encyclopedia of Chemical Technology, vol. 19, 2d Ed., New York: John Wiley & Sons, 1969, at pp. 593-607. Preferred sweeteners are noncariogenic, and particularly preferred sweeteners for use herein are xylitol, sorbitol, mannitol, sodium saccharin, and combinations thereof.

It is optional that the composition also contain a "stimulator" compound which will stimulate salivary gland secretion. A particularly preferred compound for this purpose is citric acid, present in an amount ranging from about 0.25 wt. % to about 5.0 wt. %, preferably about 0.5 wt. %. Incorporation of citric acid into the present composition also serves to provide a pleasant, citrus flavor.

It is optional that the composition contain one or more preservatives, typically an anti-oxidant present in an amount effective to retard oxidation and/or inactivation of the fluid extract. As with sweeteners, the selection of a preservative or preservatives will be readily made by one skilled in the art. Examples of suitable preservatives include ascorbyl palmitate, butylated hydroxyanisole, butylated hydroxytoluene, potassium or sodium sorbate, sodium bisulfite, sodium metabisulfite, sorbic acid, sulfur dioxide, and sodium or potassium benzoate. A particularly preferred preservative for use herein is sodium benzoate.

Other components which may, if desired, be incorporated into the present composition include coloring agents, which may be either natural or synthetic, flavoring agents, flavor preserving agents, diluting agents, emulsifying agents, excipients, pH buffering agents, and the like.

Suitable colorants include dyes that are generally suitable for food, drug and cosmetic applications, i.e., those known as F.D. & C. dyes. Acceptable dyes should be water soluble. Illustrative examples include the disodium salt of 5,5-indigotindisulfonic acid ("F.D. & C. Blue No. 2.") and the monosodium salt of 4-[4-N-ethyl-p-sulfo-benzylamino)diphenylmethylene]-1-(N-ethyl-N-p-sulfon ium-benzyl)-2,5-cyclohexadienimine ("F.D. & C. Green No. 1"). Reference may be had to the Kirk-Othmer Encyclopedia of Chemical Technology, 3rd Ed., in Volume 6, for further F.D.& C. colorants and corresponding chemical structures.

Flavorings are optional, as incorporation of citric and/or ascorbic acids into the composition will in the absence of any additional flavoring agents provide a pleasant, citrus flavor. Additional flavorings may include other natural or artificial flavors, e.g., mint oils such as peppermint, wintergreen (methyl salicylate), spearmint, eucalyptus, etc., citrus oils such as lemon oil, orange oil, lime oil, grapefruit oil, fruit essences such as apple essence, peach essence, raspberry essence, and the like. Where an oil-based flavoring agent is selected, one or more preservatives will be included in the composition as described above. Various synthetic flavors may also incorporated into the composition. The flavoring agent(s) will be present in an amount depending on the individual agent selected, but, if present, will typically range from about 0.5 wt. % to about 5.0 wt. % of the composition.

In certain embodiments the oral care composition further comprises enzymes found in saliva including lactoperoxidase, thiocyanate and glucoseoxidase.

The composition as just described is preferably administered as an aqueous solution, gel or paste and administered via a mouthspray, mouthwash, toothpaste, rinse or gel.

The composition may also be prepared as a gum or lozenge, with the preferred components and the preferred relative composition by weight the same as in the above-described aqueous solution.

In various embodiments, gum compositions are prepared using any suitable conventional method. For example, in some embodiments, the PRG4 is admixed with a chewable gum base, one or more sweeteners, and optional additional components as described hereinabove, present in the above-described proportions. In various embodiments, a gum composition described herein comprises flavoring additives, emulsifying agents, and coloring agents as described herein.

The "gum base" may be one of a number of types of compositions, and is typically prepared by heating and blending various ingredients, e.g., natural gums, synthetic resins, waxes, plasticizers, etc. Non-limiting examples of the ingredients found in a chewing gum base include masticatory substances of vegetable origin such as chicle, crown gum, nispero, rosidinha, jelutong, pendare, perillo, niger gutta, tunu, etc., masticatory substances of synthetic origin such as butadiene-styrene polymer, isobutyleneisoprene copolymer, paraffin, petroleum wax, polyethylene, polyisobutylene, polyvinylacetate, etc., plasticizers or softeners such as lanolin, stearic acid, sodium stearate, potassium stearate, glyceryl triacetate, glycerine, etc.

Waxes, including natural and synthetic waxes, petroleum waxes, paraffin waxes and microcrystalline waxes may also be incorporated into the gum base in order to obtain desirable texture and consistency.

Lozenges described herein are optionally shaped solids containing the PRG4 in a candy or glycerinated gelatin base. In some embodiments, lozenge forms are prepared, for example, using suitable methods described in Remington's Pharmaceutical Sciences. In certain instances, the PRG4 is mixed with sweetener and other optional compounds as described above, and the resulting syrup is concentrated and the mixture shaped and/or compressed, while heating, into the desired form.

The amount of PRG4 administered may vary and be dependent on the subject being treated, the severity of the xerostomia, and the judgment of the prescribing health care professional. However, an effective dosage regimen will typically be 1-2 tsp (or 1-20 mL, 2-15 mL, 3-10 mL, or the like) of an aqueous composition (or the equivalent in gum or lozenge form) given orally once or 2-6 times per day. For the aqueous composition, it is preferred that the composition be retained in contact with the oral mucosa for a time sufficient to allow coating of the interior of the mouth with the PRG4. It is preferred that the composition be retained in the mouth for 1-30, 2-20, 5-15, or 8-10 seconds. Furthermore, the composition may be, and may be administered as, a mouthwash, where the mouth is simply rinsed with the aqueous solution, or if desired, the composition may be swallowed.

In various embodiments, any oral care composition as described herein is suitable to benefit or useful for treating patients suffering from ulcerations inside the mouth, whether the common "canker sore" or the more serious ulceration often seen as a side effect of cancer therapy described as oral mucositis. The method and composition is directed to a medication that is topically administered to the lesion. In the preferred embodiment, the composition of the present invention provides prolonged relief of the pain and discomfort associated with canker sores.

In one embodiment the composition for treating oral ulcerations comprises topically administering PRG4 in an orally acceptable solution to the oral ulcer in need thereof. In another embodiment the PRG4 composition further comprises sodium hyaluronate. In yet another embodiment, the PRG4 composition further comprises one or more local anesthetics selected from the group consisting of lidocaine, lignocaine and prilocaine.

The present invention further provides a method for treating oral ulcerations comprising topically administering to the oral ulcer in need thereof, an effective amount PRG4 in a orally acceptable solution (or in any other composition envisioned herein) wherein said composition is in the form of a gel, liquid, cream, ointment, spray or viscous solution.

Surgical

Certain embodiments of the present invention provide compositions suitable for lubrication of instruments and/or other surfaces involved in surgical or medical procedures. In specific embodiments, provided herein is a viscoelastic solution (or suspension) comprising PRG4 and/or sodium hyaluronate and, optionally, additional excipients and demulcents. In some embodiments, such compositions are biocompatible aqueous solutions (or suspensions) that are very particularly suitable as surgical auxiliaries and/or temporary implants. Certain embodiments of present invention further relate to the use of said compositions (e.g., solutions) as surgical/medical lubricants for use in the insertion of catheters, endoscopes, surgical instruments, gloves into body orifices, as surgical auxiliaries and/or temporary implants, as hydration implants, and for use in cataract extraction, photokeratectomy, intraocular lens (IOL) insertion and removal, corneal surgery, glaucoma surgery, trauma surgery, posterior segment surgery, ocular plastic surgery and muscle surgery.

Generally, every surgical invasion causes tissue damage. To minimize, reduce, or prevent the damage involved, especially in areas where the tissues are particularly fragile and/or irreplaceable, viscoelastic solutions may be used as surgical auxiliaries. Such solutions protect the tissues from the surgical instruments and assist the manipulation of said tissues. They are also used for maintaining spaces or volumes to prevent tissues from coalescing and destroying such spaces or volumes. Solutions of this type are used very particularly in ophthalmic surgery.

With reference to cataract surgery, the following commercial products have thus already been proposed: Viscoat®, from Alcon Surgical, Inc., which contains sodium hyaluronate and chondroitin sulfate; this product is currently the market leader; Healon® and Healon GV®, currently marketed by A.M.O., Amvisc® and Amvisc Plus®, currently marketed by Bausch & Lomb, Vitrax®, currently marketed by A.M.O., and Viscorneal® and Biocorneal®, marketed by the Applicant, which contain sodium hyaluronate (NaHA); Orcolon®, from Optical Radiation Corporation, which contained a polyacrylamide and is now unavailable; and Occucoat®, from Storz, which contains hydroxypropyl methyl cellulose (HPMC).

In one preferred embodiment, the surgical lubricant/viscoelastic fluid is comprised of PRG4 in a surgically acceptable salt solution. In another embodiment, the surgical lubricant/viscoelastic fluid further comprises sodium hyaluronate. In yet another embodiment, the surgical lubricant/viscoelastic fluid further comprises additional excipients and demulcents, including but not limited to carboxymethylcellulose sodium, hydroxyethyl cellulose, hypromellose, methylcellulose, dextran 70, gelatin, glycerin, polyethylene glycol 300, polyethylene glycol 400, polysorbate 80, propylene glycol, polyvinyl alcohol and povidone. In yet another embodiment, the surgical lubricant/viscoelastic fluid further comprises one or more local anesthetic's selected from the group consisting of lignocaine and prilocaine.

In yet another embodiment, the surgical lubricant/viscoelastic fluid further comprises one or more antiseptics selected from the group consisting of chlorhexidine gluconate, benzalkonium chloride, cetyl trimethylammonium bromide, cetylpyridinium chloride, benzethonium chloride, alcohol, sodium chloride and sodium bicarbonate.

The present invention further provides a method of providing lubrication for use in surgical or medical procedures comprising the application of an effective amount PRG4 (e.g., in a surgically acceptable solution or in any other composition envisioned herein) to tissue or a medical device in need thereof. In specific embodiments, such methods are methods of reducing or preventing tissue damage associated with the surgical or medical procedure. Such surgical or medical procedures include the insertion of catheters, endoscopes, surgical instruments, gloves into body orifices, as surgical auxiliaries and/or temporary implants, as hydration implants, cataract extraction, photokeratectomy, intraocular lens (IOL) insertion and removal, corneal surgery, glaucoma surgery, trauma surgery, posterior segment surgery, ocular plastic surgery and muscle surgery.

Athletic Lubrication

The present invention also provides, in certain embodiments, novel compositions and methods of reducing friction during ambulatory motion, such methods comprising administering any composition (e.g., any composition comprising PRG4 protein) to a surface in need thereof (such as a chafed surface or a surface susceptible to friction and/or chafing). Athletic endeavors often include significant shear stress and friction between skin and clothing, skin and skin, and hair and skin. This often leads to chafing, "chub rub," skin lacerations, bleeding from the nipples, and so forth. This type of shear induced insult is common during long distance competitions such as marathons or ironman races. Current approaches include the application of polymers and skin moisturizers such as BODYGLIDE. However current approaches fail to provided long lasting relief and do not provide any mechanism of reducing boundary lubrication.

In certain embodiments the present invention provides an athletic composition for use in reducing friction caused by ambulatory motion comprising PRG4. In specific embodiments, the PRG4 is formulated with or in a delayed release polymer. In certain embodiments, the delayed release polymers comprises one or more of the following, carboxymethylcellulose, hydroxypropylmethylcellulose, polypropylene, or other common excipients or demulcents.

In certain embodiments, the athletic composition further comprises sodium hyaluronate.

In certain embodiments, the athletic composition further comprises Allantoin (0.5%)

In certain embodiments, the athletic composition further comprises Aloe (Aloe Barbadensis) Leaf Extract, C18 36 Acid Triglyceride, Capric/Caprylic Stearic Triglyceride, Tribehenin, and or Tocopheryl Acetate.

In one optional embodiment an adhesive patch is coated with PRG4 and is placed between the area of friction and the cause of friction. Examples of a suitable adhesive patch include band-aid or athletic tape. In another embodiment, hyaluronic acid and PRG4 are contained within the adhesive patch.

The present invention further provides a method of reducing friction during motion comprising the application of an effective amount PRG4 in a solution, gel, sol (or in any other composition or device envisioned herein) to the area in need thereof.

Dermal Filler

In one aspect, the present invention provides injectable compositions for injection into the dermis or the hypodermis (subcutaneous tissue) to restore age related tissue loss in the face, and selected areas of the body, such as neck and hands. In some instances, the use of PRG4 in a dermal filler formulation increases the amount of time the dermal filler is retained prior to absorption.

Facial aging occurs as the result of several factors, e.g.: inherent changes within the skin, effects of gravity, facial muscles acting on the skin (dynamic lines), soft tissue loss or shift and bone loss and loss of tissue elasticity. The skin ages when the epidermis begins to thin, causing the junction with the dermis to flatten. Collagen decreases as a person ages and the bundles of collagen, which gives the skin turgor, become looser and lose strength. When the skin loses elasticity, it is less able to resist stretching. Coupled with gravity, muscle pull and tissue changes, the skin begin to wrinkle Water loss and breakdown of bonds between cells also reduces the barrier function of the skin, which can cause the skin's pore size to increases.

As a person ages, the face loses volume, soft tissue, and fat. The appearance of jowls and folds are usually caused by the drooping of facial tissues and folding of areas where the muscles below are attached to the skin. As part of the reduction in soft tissue the face gets more hollow.

More specifically, in various facial areas, such as forehead, eyes, nose, midface and lower face, changes relating to aging have been well documented. In forehead area, the forehead and brow droop over time, which lowers the eyebrows and causes the upper eyelid skin to bunch. Forehead lines appear when one tries to hold the brows and eyelids up to counteract these changes. It is well known that the eyes are often the first facial feature to show signs of aging Skin changes around the eyes occur earlier than in the rest of the face since the skin is thinner around the eyes. The skin here contains fewer glands and is subjected to constant blinking, squinting, rubbing, and pulling. The midface ages when the cheeks begin to droop, causing nasolabial folds. Nasolabial folds are the lines that run from the sides of the nose to the corners of the mouth. These folds have been treated with facial fillers. In the nose area, as a person ages, the nose elongates. Common causes of elongation are thinning of the soft tissue and loss of elasticity, which causes "drooping of the tip" and unmasking of the bone, creating a new hump. In the lower face area, as the face ages, facial tissues descend. This results in the so-called "laugh lines". Folds and lines in this area have been treated with facial fillers. Further down on the face, the corners of the mouth may droop and descent of the jowls can create folds often referred to as "marionette" lines. Furthermore, jowls form when the cheeks sag around a fixed point along the jaw where the facial muscles attach to the jawbone. The facial muscles continue down into the neck as a sheet called the platysma muscle. This muscle often gaps in the center of the neck, creating two bands.

Various injectables have been used for restoring tissue loss in the face. Since the 1980s, injectable collagen has been used as a soft-tissue filler to fill wrinkles, lines and scars on the face. Collagen is a naturally occurring protein that supports various parts of the body including skin, tendons and ligaments. Fat injections have been used for years to add volume, fill wrinkles, lines and enhance the lips. Fat injections involve taking fat from one part of the patient's body (abdomen, thighs or buttocks) and reinjecting it beneath the facial skin. Botulinum toxins have been used for neck spasms, cranial nerve disorders and eye spasms. With the recent FDA approval of Botox for cosmetic use in the glabellar region, the drug is used to smooth wrinkles. When injected into facial muscles botulinum toxins block nerve impulses, temporarily paralyzing muscles and smoothing wrinkles.

Hyaluronic acid is one of most commonly used cosmetic dermal filler which adds volume to minimize wrinkles and lines. Hyaluronic acid is a linear polysaccharide that exists naturally in all living organisms and is a universal component of the extra-cellular spaces of body tissues. The identical structure of hyaluronic acid in all species and tissues makes this polysaccharide an ideal substance for use as a bio-material in health and medicine. Hyaluronic acid is present in many places in the human body. It gives volume to the skin, shape to the eyes and elasticity to the joints. The highest concentrations are found in connective tissues, and most hyaluronic acid (about 56%) is found in the skin.

Various forms of hyaluronic acid are provided commercially by a number of manufacturers. The most commonly used hyaluronic acid is the non-animal stabilized hyaluronic acid (NASHA) in a clear gel form, produced by bacterial fermentation from streptococci bacteria. Different from animal derived hyaluronic acid, the non-animal derived hyaluronic acid is free from animal proteins. This limits the risk of animal based disease transmissions or development of allergic reactions to animal proteins. The most known non-animal stabilized hyaluronic acid is manufactured by Q-med, Seminariegatan, Uppsala, and commercially available under the tradename Restylane® Since its commercialization in 1996, it is estimated that over 2,500,000 treatments have been carried out worldwide. Other non-animal stabilized hyaluronic acid products include Perlane® from Q-med, which has larger particles than Restylane®, and Captique® from Genzyme Corporation. Another commonly used filler is hyaluronan manufactured by Genzyme Corporation and commercially available under the tradename Hylaform Plus. Hylaform Plus is a sterile, nonpyrogenic, viscoelastic, clear, colorless, transparent gel implant composed of cross-linked molecules of hyaluronan. Although hyaluronic acid and derivatives are the most commonly used dermal fillers, they have limited viability. The re-injection is needed every 4 to 12 months, or even shorter. This is main drawback of HA dermal fillers.

In one embodiment, the injectable composition comprises PRG4 in a viscous solution. In one further embodiment, the injectable composition comprises PRG4 in combination with a dermatologically effective amount of hyaluronic acid. In yet another embodiment, the injectable composition comprises PRG4 in combination with a dermatologically effective amount of collagen, carboxymethyl cellulose, polyethylene glycol and/or polyethylene oxide. In one further embodiment, the injectable composition comprises PRG4 in combination with a drug selected from the group consisting of antithrombogenic drugs, anti-inflammatory drugs, hormones, chemotactic factors, analgesics, growth factors, cytokines, osteogenic factors and anesthetics. In one further embodiment, the injectable composition comprises PRG4 in combination with retinoic acid and/or deuterium reduced water.

A treatment method for restoring of tissue volume, skin turgor, texture and tightness in the face or selected areas of the body of a person comprising the steps of injecting a composition of PRG4 (or other dermal composition envisioned herein) into the dermis, or the hypodermis at one or more areas of the face, or selected areas of the body of a person In another embodiment the areas of treatment include the peri-orbital area, the lips, the malar area, the nasolabial folds, the labio-mandibular folds, the neck, or the hands.

Drug Delivery

In certain embodiments, present invention provides a method of drug delivery, the method comprising a bioactive agent in combination with (e.g., admixed) with PRG4 protein. In some embodiments, a bioactive agent is delivered to a subject, and delivered in a composition comprising: a bioactive agent admixed with a carrier comprising PRG4.

Carrier materials for drug delivery of pharmaceuticals are based on a broad range of materials, such as organic or inorganic polymers, metals and ceramics. Without being bound to any theory it is believed that the use of PRG4 as a drug delivery method will result in increased residence time and superior localization of target compounds.

In one embodiment the bioactive agent comprises a drug, a peptide, a protein, an antibody or fragment thereof, a nucleic acid, or imaging agent. In another embodiment, the delivery carrier further comprises sodium hyaluronate. In yet another embodiment, the delivery carrier further comprises a surface active phospholipid selected from the group consisting of L-α-dipalmitoylphosphatidylcholine, phosphatidylcholine, phosphatidylethanolamine and sphingomyelin.

The physical delivery of the admixture can be accomplished via by topical administration, injection, or orally.

Lubrication for Breastfeeding

In some embodiments, the present invention provides a method of lubrication for nursing mothers, said method comprising administering to a surface in need thereof PRG4 protein. During nursing, incomplete latching can cause significant shear stress between the palette of the baby's mouth and the mother's nipple. Over time, the nipples become inflamed and sore. Existing approaches, such as lanolin ointment or gel patches, can only be used for a limited time and may be messy or irritate the nipple for certain people, since the mechanism is fluid film lubrication. PRG4 boundary lubrication, which operates in a single monolayer, offers superior residence time without the residue that other creams create. In certain embodiements the combination of both fluid film and boundary lubrication may be useful.

In one preferred embodiment, the nursing lubricant is comprised of PRG4 in an aqueous solution, gel, sol, or adhesive patch. In another embodiment, the lubricant further comprises sodium hyaluronate. In yet another embodiment, the lubricant comprises additional excipients and demulcents.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

As used herein, the term "PRG4", "PRG4 protein" or "proteoglycan 4" protein, is used interchangeably with the term "lubricin" protein. PRG4 is used herein also to encompass the term megakaryocyte stimulating factor (MSF), that has been accepted for the UCL/HGNC/HUGO Human Gene Nomenclature data base, and superficial zone protein (SZP). The PRG4 or lubricin protein (used interchangeably herein with lubricin proteoglycan) as used herein refers to any isolated or purified native or recombinant lubricin proteins, homologs, functional fragments or motifs, isoforms, and/or mutants thereof. In certain embodiments, the isolated or purified PRG4 protein comprises an amino acid sequence for a human native or recombinant lubricin protein. In other embodiments, the isolated or purified PRG4 protein comprises an amino acid sequence encoded by prg4 gene exons that encode the full length PRG4 protein or isoforms' primary structures. The proteoglycan 4 (prg4) gene contains 12 exons. The PRG4 protein used herein comprises an amino acid sequence encoded by prg4 gene exons 1-12, more preferably, exons 6-12, and most preferably, exons 9-12.

As used herein, the PRG4 protein includes any PRG4 proteins now known, or later described. In certain embodiments, a preferred PRG4 protein amino acid sequence is provided in SEQ ID NO:1. The PRG4 protein shares the primary amino acid structure of any known PRG4 proteins or isoforms with at least 60% homology, preferably 75% homology, more preferably 85%, 90%, 95%, 96%, 97%, 98%, 99% or more homology. In certain embodiments, a preferred PRG4 protein has an average molar mass of between 50 kDa and 400 kDa, comprising one or more biological active portions of the PRG4 protein, or functional fragments, such as a lubricating fragment, or a homolog thereof.

As used herein, the PRG4 protein comprises a biological active portion of the protein. As used herein, a "biologically active portion" of the PRG4 protein includes a functional fragment of a protein comprising amino acid sequences sufficiently homologous to, or derived from, the amino acid sequence of the protein, which includes fewer amino acids than the full length protein, and exhibits at least one activity of the full-length protein. Typically a biologically active portion comprises a functional domain or motif with at least one activity of the protein. A biologically active portion of a protein can be a polypeptide which is, for example, 10, 25, 50, 100, 200, or more amino acids in length. In one embodiment, a biologically active portion of the PRG4 protein can be used as a therapeutic agent alone or in combination with other therapeutic agents for treating undesirable or decreased vaginal boundary lubrication.

In yet another embodiment, functional fragments, multimers (e.g., dimers, trimers, tetramers, etc.), homologs or orthologs of PRG4 are used in the oral care composition. Functional fragments and homologs of PRG4 include those with fewer repeats within the central mucin-like KEPAPTT-repeat domain (SEQ ID NO:4), glycosylated and non-glycosylated forms of the protein, splice variants, recombinant forms, and the like. A lubricating fragment of PRG4 exhibits at least 20%, 30%, 40%, 50%, 60%, 70%, 80%, 90%, or 95% of the lubricating effect of human PRG4, as measured qualitatively, mechanically, optically, electrically, or by biochemical assay.

The nucleic acid and amino acid sequences of several native and recombinant PRG4 or lubricin proteins, and characterization of the PRG4 proteins and various isoforms are disclosed in, for instance, U.S. Pat. Nos. 5,326,558; 6,433,142; 7,030,223; 7,361,738 to Turner et al., and U.S. Pat. Nos. 6,743,774 and 6,960,562 to Jay et al. U.S. Publication No. 20070191268 to Flannery et al. also discloses recombinant PRG4 or lubricin molecules useful in the present invention.

Methods for isolation, purification, and recombinant expression of a PRG4 protein are well known in the art. In certain embodiments, the method starts with cloning and isolating mRNA and cDNA encoding PRG4 proteins or isoforms using standard molecular biology techniques, such as PCR or RT-PCR. The isolated cDNA encoding the PRG4 protein or isoform is then cloned into an expression vector, and further transformed and expressed in a host cell for producing recombinant PRG4 protein.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising an active domain of the PRG4 gene and a nucleic acid sequence amplified using a primer of the invention.

In certain embodiments, the PRG4 protein encoding nucleic acid may contain one or more mutations, deletions, or insertions. In such embodiments, the PRG4 protein encoding nucleic acid is at least 60% homology, preferably 75% homology, more preferably 85%, 90%, 95%, 96%, 97%, 98%, 99%, or more homology, to a wild type PRG4 protein encoding nucleic acid.

As used herein, the term "'cDNAs" includes DNA that is complementary to mRNA molecules present in a cell or organism mRNA that can be converrted into cDNA with an enzyme such as reverse transcriptase. In certain embodiments, the cDNA encoding PRG4 protein is isolated from PRG4 mRNA expressed in human corneal or conjunctival epithelial cells using an RT-PCR method well known in the art.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of thymine when the polynucleotide is RNA, instead of DNA. This alphabetical representation can be inputted into databases in a computer and used for bioinformatics applications such as, for example, functional genomics and homology searching.

As used herein, the term "isolated polynucleotide/cDNA" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule encoding the PRG4 protein used in the invention can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "native or naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In certain embodiments, the PRG4 protein used herein refers to PRG4 proteins or various homologs or isoforms thereof, that are naturally or recombinantly expressed in humans or other host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" can be any cells that express a human PRG4 protein.

As used herein, "homologs" are defined herein as two nucleic acids or peptides that have similar, or substantially identical, nucleic acids or amino acid sequences, respectively. The term "homolog" further encompasses nucleic acid molecules that differ from one of the nucleotide sequences due to degeneracy of the genetic code and thus encodes the same amino acid sequences. In one of the preferred embodiments, homologs include allelic variants, orthologs, paralogs, agonists, and antagonists of nucleic acids encoding the PRG4 protein (e.g., SEQ ID NO:1, see, e.g., FIG. 2).

As used herein, the term "orthologs" refers to two nucleic acids from different species, but that have evolved from a common ancestral gene by speciation. Normally, orthologs encode peptides having the same or similar functions. In particular, orthologs of the invention will generally exhibit at least 80-85%, more preferably 85-90% or 90-95%, and most preferably 95%, 96%, 97%, 98%, or even 99% identity, or 100% sequence identity, with all or part of the amino acid sequence of any known PRG4 proteins (e.g., SEQ ID NO:1), isoforms, or analogs thereof, and will exhibit a function similar to these peptides. As also used herein, the term "paralogs" refers to two nucleic acids that are related by duplication within a genome. Paralogs usually have different functions, but these functions may be related.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions ×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence of any known PRG4 protein (e.g., SEQ ID NO:1).

In certain embodiments, an isolated nucleic acid homolog encoding the PRG4 protein comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence encoding amino acid sequences of such PRG4 protein (e.g., SEQ ID NO:1).

The determination of the percent sequence identity between two nucleic acid or peptide sequences is well known in the art. For instance, the Vector NTI 6.0 (PC) software package (InforMax, Bethesda, Md.) to determine the percent sequence identity between two nucleic acid or peptide sequences can be used. In this method, a gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Furthermore, the PRG4 protein used herein includes PRG4 protein encoded by a polynucleotide that hybridizes to the polynucleotide encoding PRG4 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding PRG4 protein described herein. As used herein, the term "stringent conditions" refers to hybridization overnight at 60° C. in 10× Denhart's solution, 6×SSC, 0.5% SDS, and 100 mg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in certain embodiments, the phrase "stringent conditions" refers to hybridization in a 6×SSC solution at 65° C. In other embodiments, "highly stringent conditions" refer to hybridization overnight at 65° C. in 10×Denhart's solution, 6×SSC, 0.5% SDS and 100 mg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are well known in the art. Accordingly, the PRG4 proteins encoded by nucleic acids used herein include nucleic acid having at least 60% homology, preferably 75% homology, more preferably 85%, more preferably 90%, most preferably 95%, 96%, 97%, 98%, 99% homology to a polynucleotide sequence that encodes a human PRG4 protein (e.g., SEQ ID NO:1) or a specific isoform or homolog thereof.

Moreover, the PRG4 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In certain embodiments of the present invention, the chimeric protein is a chimera of PRG4 protein with other PRG4 protein isoforms.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In certain embodiments, the language "substantially free of cellular material" includes preparations of a PRG4 protein having less than about 30% (by dry weight) of other proteins (also referred to herein as a "contaminating protein"), more preferably less than about 20%, still more preferably less than about 10%, and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

Other features and advantages of the invention will be apparent from the following description of the preferred embodiments thereof and from the claims. These and many other variations and embodiments of the invention will be apparent to one of skill in the art upon a review of the description and examples.

EXAMPLES

Example 1

Treatment of Deficient Oral Cavity Boundary Lubrication In Vivo

Xerostomia

A mouthrinse composition suitable for use as an oral lubricant has the following composition:

| PRG4 Mouthrinse Solution: | |
| --- | --- |
| PRG4 | 100 µg/mL |
| Sorbital | 2% |
| Glycerin | 15% |
| Benzoic Acid | 0.02% |
| FD&C Green No. 3 dye | q.s |
| Peppermint Oil Flavoring | q.s. |
| Sterile Water | q.s. |

A mouthrinse of the above formula is made by mixing together the ingredients listed above to make a finished product suitable for use in lubricating the oral cavity.

Administration: 20 ml of a mouthrinse of the above formula is administered to a patient suffering from Xerostomia every four hours or as needed. The patient is to gargle with the mouthrinse for 2 to 5 minutes and completely spit the rinse.

A chewing gum suitable for delivery of PRG4 to the oral cavity has the following composition:

| PRG4 Chewing Gum: | |
| --- | --- |
| PRG4 | 50 µg/chewing gum tablet (~5%) |
| Sorbital/Mannitol Mixture (50:50) | 30% |
| Mint Flavoring | q.s. |
| Sucralose | 2% |
| Chicle Gum Base | 20% |
| Starch | 10% |
| Talc | 30% |

A chewing gum of the above formula is made by mixing together the ingredients listed above to make a finished product that is effective in relieving the symptoms of dry mouth. Briefly, the formulations are prepared by first melting the gum base at a temperature from 82° to 95° C. and mixing the gum base in a kettle with the sorbitol/mannitol, starch and other ingredients wherein mixing was continued for several minutes and thereafter the flavor and artificial sweeteners were mixed into the mixture for approximately 4 minutes. After cooling to a suitable temperature, PRG4 is added to the mixture. The mixture is then discharged and formed into slabs.

Clinical Study: A randomized, double blind study is conducted to determine the effectiveness of the PRG4 chewing gum in comparison with chewing gum without PRG4. Individuals suffering from Xerostomia are invited to a test panel. The panelists chew either PRG4 chewing gum or a gum that does not contain PRG4. A questionnaire is distributed to the panelists who then record their experiences including observations concerning the amount of increase in salivation experienced.

Example 2

Treatment of Oral Mucositis in a Cancer Patient

A concentrated bioadherent oral gel suitable for delivery of PRG4 to the oral cavity has the following composition:

| PRG4 Oral Gel: | |
| --- | --- |
| PRG4 | 10% |
| Saccharin Sodium | 2% |
| Flavoring | q.s. |
| Sodium Hyaluronate | 5% |
| PEG-40 Hydrogenated Castor Oil | 10% |
| Polyvinylpyrrolidone (PVP) | 15% |
| Sodium Benzoate | 0.02% |

-continued

| PRG4 Oral Gel: | |
|---|---|
| Propylene Glycol | 30% |
| Water | q.s. |

A concentrated bioadherent oral gel of the above formula is made by mixing together the ingredients listed above to make a finished product that is effective in relieving the symptoms of oral mucositis. The above components are mixed together and allowed to dry into a solid form. The solid form is then ground into fine powder.

Preparation and administration: 15 g of the powder is mixed with 5 ml of water in a glass. If the resultant solution is too thick, additional water may be added to achieve a desired thickness. The resultant solution is than rinsed around the mouth of an individual suffering from oral mucositis for at least 2 minutes or as needed to coat tongue, palate, throat, inside of cheeks and all oral tissue thoroughly. After rinse, the solution is spit out. Dosing is three times a day or as needed.

Example 3

Use of PRG4 in Cataract Surgery

A viscoelastic composition suitable for delivery of PRG4 to the eye has the following composition:

| PRG4 Viscoelastic Composition: | |
|---|---|
| PRG4 | .1-2% |
| Sodium Chondroitin Sulfate | 4% |
| Hyaluronic Acid (Sodium Salt) | 3% |
| Sodium Chloride | 0.5% |
| Dibasic Sodium Phosphate | 0.3% |
| Monobasic Sodium Phosphate (monohydrate) | 0.04% |
| Water | q.s. |
| HCl/NaOH | for adjusting to pH 7 |

A viscoelastic composition of the above formula is made by mixing together the ingredients listed above to make a finished product that is suitable for use as a surgical aid in anterior segment procedures including cateract extraction and intraocular lens implantation. The composition is packaged in a syringe assembly with a 27-gauge cannula.

Application: For cataract surgery and intraocular lens implantation, the PRG4 viscoelastic solution is carefully introduced into the anterior chamber. The PRG4 viscoelastic solution may be injected into the chamber prior to or following delivery of the crystalline lens. Optionally, instillation of the PRG4 viscoelastic solution prior to lens delivery protects the corneal endothelium from possible damage arising from surgical instrumentation during the cataract extraction surgery. The PRG4 viscoelastic solution can also be used to coat an intraocular lens as well as the tips of surgical instruments prior to implantation surgery. Additional solution may be injected during anterior segment surgery to fully maintain the chamber or replace any solution lost during the surgical procedure. At the end of the procedure, on may be removed from the eye by thoroughly irrigating and aspirating with a balanced salt solution. Alternatively, the PRG4 viscoelastic solution may be left in the eye.

Example 4

Reduction of Friction During Marathon

A anti-chafing skin protectant cream containing PRG4 has the following composition:

| PRG4 Anti-chafing Skin Protectant Cream: | |
|---|---|
| PRG4 | 2-4% |
| Caprylic/Capric Triglyceride | 20% |
| Glycerin | 8% |
| Pentylene Glycol | 5% |
| Allantoin | 0.5% |
| Coconut Oil | 3.5% |
| Shea Butter | 1.5% |
| Hydroxypropylmethylcellulose (HPMC) | 0.5% |
| Ceramide | 0.2% |
| Xanthan Gum | 0.1% |
| Water | q.s. |

An anti-chafing skin protectant cream of the above formula is made by first mixing together the pentylene glycol, glycerin, and water. The HPMC is slowly added and homogenized to avoid foaming to form an aqueous phase. PRG4 is added to the aqueous phase. An oil phase is prepared by mixing the Caprylic/Capric Triglyceride, Shea Butter, Coconut Oil, and Xanthan Gum while heating to a temperature of about 42° C. While stirring, the aqueous phase is quickly added to the oil phase under vacuum and the resultant mixture is emulsified.

Application: Prior to engaging in an athletic activity, the anti-chafing skin protectant is applied to areas of the skin with high shear stress, including but not limited to, groin areas, waistband areas, thighs, nipples, underarms, bra areas, buttocks, feet, and other areas of friction between skin and clothing, skin and skin, and/or skin and hair. Reapplication is every hour or as needed.

Example 5

Treatment of Peri-Orbital Wrinkles

An aqueous solution containing PRG4 has the following composition:

| PRG4 Solution: | |
|---|---|
| PRG4 | 1 mg/ml |
| Hyaluronic Acid | 20 mg/ml |
| Phosphate buffered Saline pH 7.0 | q.s. |

An aqueous solution of the above formula is made by mixing together the ingredients listed above to make a finished product that is suitable for injection.

Clinical Study: A 12-week randomized, double-blinded controlled clinical study evaluates the effectiveness of bi-weekly PRG4/hyaluronic acid injectable solution in comparison to a 20 mg/ml hyaluronic acid injection alone and placebo.

150 patients with moderate to severe peri-orbital wrinkles are enrolled. Wrinkle severity is evaluated with a five-step validated Wrinkle Severity Rating Scale (WSRS) (i.e., none, mild, moderate, severe, extreme) by an on-site blinded evaluator.

Primary endpoint: The primary study endpoint was wrinkle severity 12 weeks after optimal correction was achieved. Patient success is defined as maintaining at least one point improvement on the WSRS at 12 weeks after optimal correction is achieved.

Secondary endpoint: WSRS is assessed at 2, 6 and 24 weeks after optimal correction.

Safety assessments include collection of patient symptoms in a 14 day diary, investigator evaluation of adverse eperiences at 72 hours, and at 2, 6, 12 and 24 weeks and development of humoral or cell-mediated immunity.

Example 6

Transdermal Drug Delivery

A 3% Diclofenac Gel containing PRG4 has the following composition:

| 3% Diclofenac Gel | |
|---|---|
| Diclofenac Sodium | 3% |
| PRG4 | 2% |
| Polyethylene glycol monomethyl ether | 20% |
| Benzyl Alcohol | 0.01% |
| Water | q.s. |

An Diclofenac gel in a PRG4 carrier of the above formula is made by mixing together the ingredients listed above to make a finished product that is suitable for topical administration.

Clinical Study: A 12-week randomized, double-blinded controlled clinical study evaluates the effectiveness of Diclofenac in PRG4 carrier gel in comparison to a gel vehicle alone on actinic keratoses (AK).

200 patients with no fewer than five AK lesions in a major body area, defined as a 5 cm by 5 cm region of the scalp, forehead, face, forehead and hand. Patients undergo a 60 day washout from disallowed medications (masoprocol, 5-fluorouracil, retinoids, cyclosporine, etc.).

Patients are instructed to apply the Diclofenac gel onto the affect skin over the lesion. At the end of treatment study, complete clearance of actinic keratosis lesions is evaluated. A follow-up evaluation is given 30 days post-treatment.

Example 7

Lubrication during Nursing

A lubricating cream containing PRG4 has the following composition:

| PRG4 Lubricating cream | |
|---|---|
| PRG4 | 2-5% |
| Mallow Root | 2% |
| Coconut Oil | 10% |
| Shea Butter | q.s. |

A lubricating cream containing PRG4 of the above formula is made by mixing together the ingredients listed above to make a finished product that is suitable for topical administration.

Application: A lubricating cream containing PRG4 is applied to areas of sensitivity, pain or dryness subsequent to breastfeeding.

What is claimed is:

1. A method for treating decreased oral cavity boundary lubrication or disorder or symptoms associated therewith, or a improving oral cavity boundary lubrication in a patient in need thereof, comprising administering to the patient a composition comprising an effective amount or concentration of proteoglycan 4 (PRG4) having at least 95% primary amino acid sequence homology with the amino acid sequence of SEQ ID NO:1.

2. The method of claim 1, wherein the PRG4 is formulated in an aqueous, osmotically balanced salt solution; multiphasic emuslion; gel; liquid; cream; ointment; spray; paste; viscous solution; slow-release device; lozenge; or gum.

3. The method of claim 1, wherein the disorder or symptoms associated with decreased oral cavity boundary lubrication are selected from the group consisting of oral ulceration, xerostomia, Sjogren's syndrome; allergy; oral surface disorders; chronic inflammation; hyperosmolarity; aging; or nerve damage; side effects associated with prescription or over-the-counter drugs, radiation therapy, or chemotherapy; and any combinations thereof.

4. The method of claim 1, wherein the composition further comprises one or more of:
   (a) sodium hyaluronate or hyaluronic acid;
   (b) about 0.25 wt. % to 10 wt. % eriodictyon fluid extract;
   (c) about 1.0 wt. % to 30 wt. % sweetener or flavoring agent;
   (d) a stimulator compound selected from the group consisting of citric acid, ascorbic acid, and mixtures thereof, in an amount effective to stimulate salivary gland secretion;
   (e) one or more local anaesthetics selected from the group consisting of lidocaine, lignocaine, and prilocalne; and/ or
   (f) one or more enzymes found in saliva selected from the group consisting of lactoperoxidase, thiocyanate, or glucoseoxidase.

5. The method of claim 1, wherein the composition futher comprising a gum base and one of more of:
   (a) about 0.25 wt. % to 10 wt. % eriodictyon fluid extract, citrus oil, lemon oil, lime oil, neroli oil, orange oil, a mint oil, peppermint oil, spearmint oil, anise oil, cardamom oil, cinnamon oil, clove oil, coriander oil, eucalyptus oil, fennel oil, lemongrass oil, nutmeg oil, eriodictyon fluid extract, or glycyrrhiza extract;
   (b) about 1.0 wt. % to 30 wt. % sweetener or flavoring agent;
   (c) a stimulator compound selected from the group consisting of citric acid, ascorbic acid, and mixtures thereof, in an amount effective to stimulate salivary gland secretion; and
   (d) a therapeutically effective amount of sodium hyaluronate.

6. The method of claim 1, wherein the composition is a lozenge composition comprising a shaped solid, the comprising further comprising one or more of the following:

(a) about 0.25 wt. % to 10 wt. % eriodictyon fluid extract;
(b) about 1.0 wt. % to 30 wt. % sweetener;
(c) a stimulator compound selected from the group consisting of citric acid, ascorbic acid, and mixtures thereof, in an amount effective to stimulate salivary gland secretion; and
(d) a gelatin base; and
(e) a therapeutically effective amount of sodium hyaluronate.

7. The method of claim 1, wherein the PRG4 is at a concentration of 10-100,000 μg/mL.

8. The method of claim 1, wherein the PRG4 is an isolated or purified native PRG4.

9. The method of claim 1, wherein the PRG4 is a recombinant PRG4.

10. The method of claim 1, wherein the PRG4 is human PRG4.

11. The method of claim 1, wherein the PRG4 has the amino acid sequence of SEQ ID NO:1.

12. The method of claim 4, wherein the sodium hyaluronate or hyaluronic acid is at a concentration of 10-100,000 μg/mL.

* * * * *

UNITED STATES PATENT AND TRADEMARK OFFICE
CERTIFICATE OF CORRECTION

PATENT NO. : 9,730,865 B2
APPLICATION NO. : 13/321532
DATED : August 15, 2017
INVENTOR(S) : Benjamin Sullivan et al.

Page 1 of 1

It is certified that error appears in the above-identified patent and that said Letters Patent is hereby corrected as shown below:

In the Claims

In Claim 3, at Column 33, Lines 56-57, replace "oral ulceration, xerostomia, Sjogren's syndrome" with --oral ulceration; xerostomia; Sjogren's syndrome--.

In Claim 3, at Column 33, Line 59, replace "or nerve damage" with --nerve damage--.

In Claim 4, at Column 34, Lines 44-45, replace "and/or" with --and--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

| | |
|---|---|
| PATENT NO. | : 9,730,865 B2 |
| APPLICATION NO. | : 13/321532 |
| DATED | : August 15, 2017 |
| INVENTOR(S) | : Sullivan et al. |

It is certified that error appears in the above-identified patent and that said Letters Patent is hereby corrected as shown below:

In the Specification

At Column 1, Line 17 before the heading "FIELD OF THE INVENTION," please insert the following heading and paragraph:
--STATEMENT REGARDING FEDERALLY SPONSORED RESEARCH OR DEVELOPMENT
This invention was made with government support under EY005612 awarded by the National Institutes of Health. The government has certain rights in the invention.--

Signed and Sealed this
Second Day of May, 2023

Katherine Kelly Vidal
Director of the United States Patent and Trademark Office

SEQUENCE LISTING

```
<160> NUMBER OF SEQ ID NOS: 4

<210> SEQ ID NO 1
<211> LENGTH: 1404
<212> TYPE: PRT
<213> ORGANISM: Homo sapiens

<400> SEQUENCE: 1

Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
        50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
        130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175
```

-continued

```
Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
            245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
            275                 280                 285

Thr Thr Thr Thr Asn Lys Gln Thr Ser Thr Asp Gly Lys Glu Lys Thr
            290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
            325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
            370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
            405                 410                 415

Thr Lys Glu Pro Ala Pro Thr Thr Thr Lys Ser Ala Pro Thr Thr Pro
            420                 425                 430

Lys Glu Pro Ala Pro Thr Thr Pro Lys Lys Pro Ala Pro Thr Thr Pro
            435                 440                 445

Lys Glu Pro Ala Pro Thr Thr Pro Lys Glu Pro Thr Pro Thr Thr Pro
450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
            485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
            515                 520                 525

Ser Ala Pro Thr Thr Thr Lys Glu Pro Ala Pro Thr Thr Thr Lys Ser
            530                 535                 540

Ala Pro Thr Thr Pro Lys Glu Pro Ser Pro Thr Thr Lys Glu Pro
545                 550                 555                 560

Ala Pro Thr Thr Pro Lys Glu Pro Ala Pro Thr Thr Pro Lys Lys Pro
            565                 570                 575

Ala Pro Thr Thr Pro Lys Glu Pro Ala Pro Thr Thr Pro Lys Glu Pro
            580                 585                 590
```

```
Ala Pro Thr Thr Thr Lys Lys Pro Ala Pro Thr Thr Pro Lys Glu Pro
            595                 600                 605
Ala Pro Thr Thr Pro Lys Glu Thr Ala Pro Thr Thr Pro Lys Lys Leu
            610                 615                 620
Thr Pro Thr Thr Pro Glu Lys Leu Ala Pro Thr Thr Pro Glu Lys Pro
625                 630                 635                 640
Ala Pro Thr Thr Pro Glu Glu Leu Ala Pro Thr Thr Pro Glu Glu Pro
                645                 650                 655
Thr Pro Thr Thr Pro Glu Glu Pro Ala Pro Thr Thr Pro Lys Ala Ala
            660                 665                 670
Ala Pro Asn Thr Pro Lys Glu Pro Ala Pro Thr Thr Pro Lys Glu Pro
            675                 680                 685
Ala Pro Thr Thr Pro Lys Glu Pro Ala Pro Thr Thr Pro Lys Glu Thr
            690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
Thr Pro Lys Gly Thr Ala Pro Thr Thr Pro Lys Glu Pro Ala Pro Thr
            755                 760                 765
Thr Pro Lys Glu Pro Ala Pro Thr Thr Pro Lys Gly Thr Ala Pro Thr
            770                 775                 780
Thr Leu Lys Glu Pro Ala Pro Thr Thr Pro Lys Lys Pro Ala Pro Lys
785                 790                 795                 800
Glu Leu Ala Pro Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
            835                 840                 845
Thr Pro Pro Pro Thr Thr Ser Glu Val Ser Thr Pro Thr Thr Thr Lys
            850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
            900                 905                 910
Thr Thr Ala Lys Asp Lys Thr Thr Glu Arg Asp Leu Arg Thr Thr Pro
            915                 920                 925
Glu Thr Thr Thr Ala Ala Pro Lys Met Thr Lys Glu Thr Ala Thr Thr
            930                 935                 940
Thr Glu Lys Thr Thr Glu Ser Lys Ile Thr Ala Thr Thr Gln Val
945                 950                 955                 960
Thr Ser Thr Thr Thr Gln Asp Thr Thr Pro Phe Lys Ile Thr Thr Leu
                965                 970                 975
Lys Thr Thr Thr Leu Ala Pro Lys Val Thr Thr Thr Lys Lys Thr Ile
                980                 985                 990
Thr Thr Thr Glu Ile Met Asn Lys  Pro Glu Glu Thr Ala  Lys Pro Lys
            995                 1000                 1005
```

```
Asp Arg Ala Thr Asn Ser Lys Ala Thr Thr Pro Lys Pro Gln Lys
    1010                1015                1020

Pro Thr Lys Ala Pro Lys Lys Pro Thr Ser Thr Lys Lys Pro Lys
    1025                1030                1035

Thr Met Pro Arg Val Arg Lys Pro Lys Thr Thr Pro Thr Pro Arg
    1040                1045                1050

Lys Met Thr Ser Thr Met Pro Glu Leu Asn Pro Thr Ser Arg Ile
    1055                1060                1065

Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110

Phe Met Pro Glu Val Thr Pro Asp Met Asp Tyr Leu Pro Arg Val
    1115                1120                1125

Pro Asn Gln Gly Ile Ile Ile Asn Pro Met Leu Ser Asp Glu Thr
    1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380
```

```
Thr Ala  Arg Ala Ile Thr Thr  Arg Ser Gly Gln Thr  Leu Ser Lys
    1385              1390                   1395

Val Trp  Tyr Asn Cys Pro
    1400

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcagggt accccaaa                                                 18

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagactttgg ataaggtctg cc                                            22

<210> SEQ ID NO 4
<211> LENGTH: 7
<212> TYPE: PRT
<213> ORGANISM: Homo sapiens

<400> SEQUENCE: 4

Lys Glu Pro Ala Pro Thr Thr
1               5
```